United States Patent [19]
Anderson

[11] Patent Number: 5,263,110
[45] Date of Patent: Nov. 16, 1993

[54] IMAGING ENDOSCOPE AND ENDOSCOPIC METHOD EMPLOYING PHASE CONJUGATE IMAGING TECHNIQUES

[75] Inventor: John E. Anderson, Blacksburg, Va.

[73] Assignee: Linvatec Corporation, Largo, Fla.

[21] Appl. No.: 939,471

[22] Filed: Sep. 3, 1992

[51] Int. Cl.⁵ .......................................... G02B 23/26
[52] U.S. Cl. ................................. 385/117; 359/435;
                                              359/737; 385/119; 385/902
[58] Field of Search .......................... 385/115-119,
         385/33, 902; 128/4-9; 606/15-17; 359/300,
                             367, 434, 435, 735-737, 784, 797

[56]         References Cited
         U.S. PATENT DOCUMENTS

| | | | |
|---|---|---|---|
| 3,257,902 | 6/1966 | Hopkins | 359/435 |
| 4,025,155 | 5/1977 | Imai | 359/435 |
| 4,138,192 | 2/1979 | Yamasita | 359/726 |
| 4,165,917 | 8/1979 | Yamasita et al. | 359/784 |
| 4,168,882 | 9/1979 | Hopkins | 359/434 |
| 4,195,904 | 4/1980 | Yamashita | 359/367 |
| 4,354,730 | 10/1982 | Bel | 359/434 |
| 4,500,855 | 2/1985 | Feinberg | 359/300 |
| 4,750,818 | 6/1988 | Cochran | 359/300 |
| 4,755,029 | 7/1988 | Okabe | 359/654 |
| 4,895,790 | 1/1990 | Swanson et al. | 430/321 |
| 4,921,333 | 5/1990 | Brody et al. | 359/15 |
| 4,927,251 | 5/1990 | Schoen | 359/364 |
| 4,928,695 | 5/1990 | Goldman et al. | 128/642 |
| 4,938,596 | 7/1990 | Gauthier et al. | 356/360 |
| 4,945,239 | 7/1990 | Wist et al. | 250/358.1 |
| 4,964,710 | 10/1990 | Leiner | 359/434 |
| 4,994,664 | 2/1991 | Veldkamp | 250/216 |
| 5,018,852 | 5/1991 | Cheng et al. | 356/28.5 |
| 5,040,869 | 8/1991 | Poisel et al. | 385/115 |
| 5,059,917 | 10/1991 | Stephens | 359/347 |
| 5,074,860 | 12/1991 | Gregory et al. | 385/117 X |

OTHER PUBLICATIONS

Photorefractive Phase Conjugators, Yeh, Fellow, IEEE, Proc of vol. 80, No. 3, Mar. 1992, pp. 436-449.
Binary Optics, Veldkamp et al, Scientific American, May 1992, pp. 92-97.
Optical Phase Conjugation, Shkunov et al, Scientific American, Dec. 1985, pp. 54-59.

Primary Examiner—John D. Lee

[57]              ABSTRACT

An improved endoscope employing phase conjugate imaging principles includes a first transmissive member for transmitting light rays received at a distal tip of the endoscope to an intermediate filter location. A phase conjugate filter at the intermediate filter location redirects the rays, according to the precise inverse of their incoming direction, along a second transmissive member optically identical to the first. Rays exiting the endoscope bear the exact relation to one another as when entering the tip of the endoscope and may be imaged or displayed on an eyepiece or video screen.

20 Claims, 2 Drawing Sheets

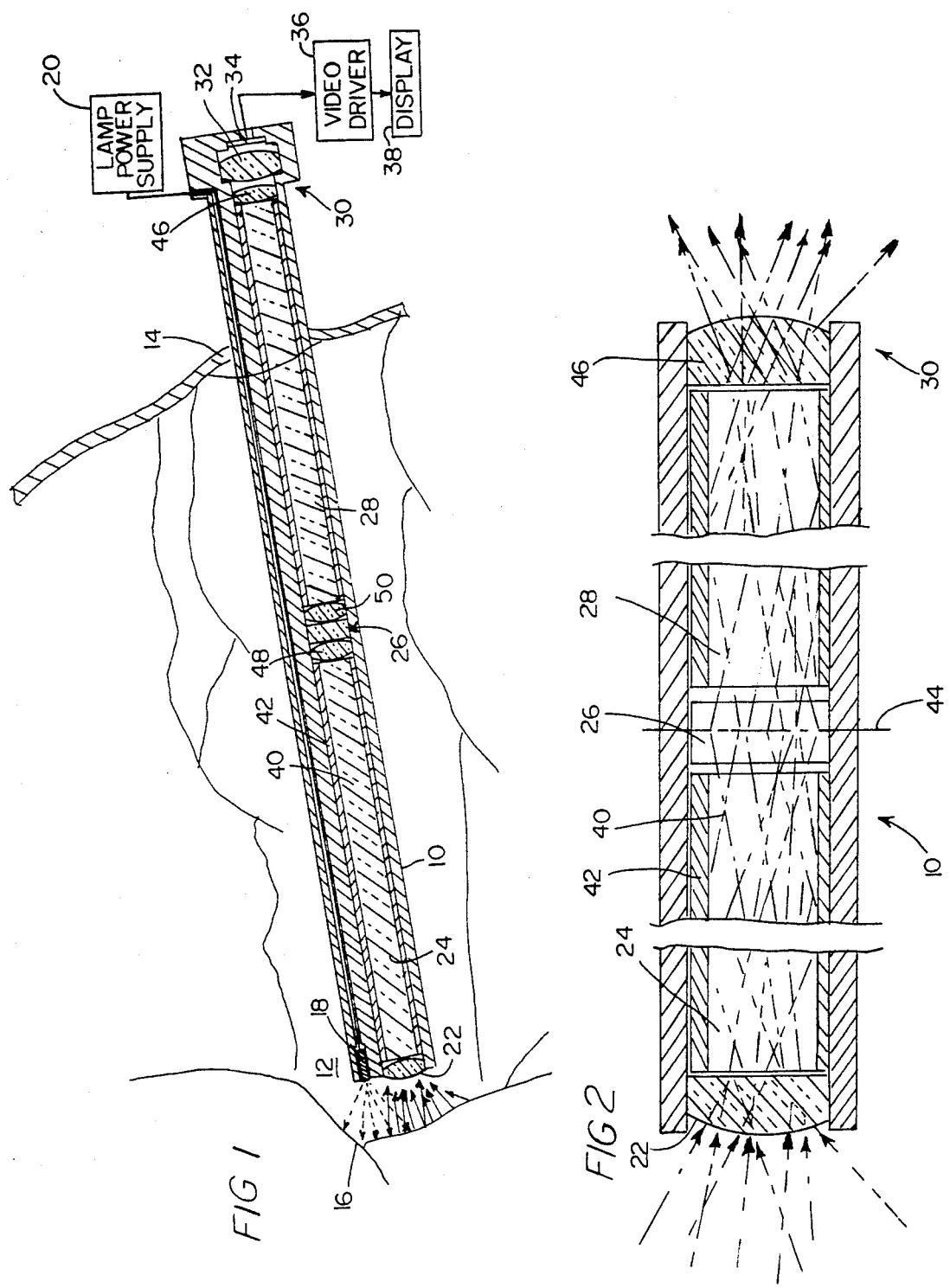

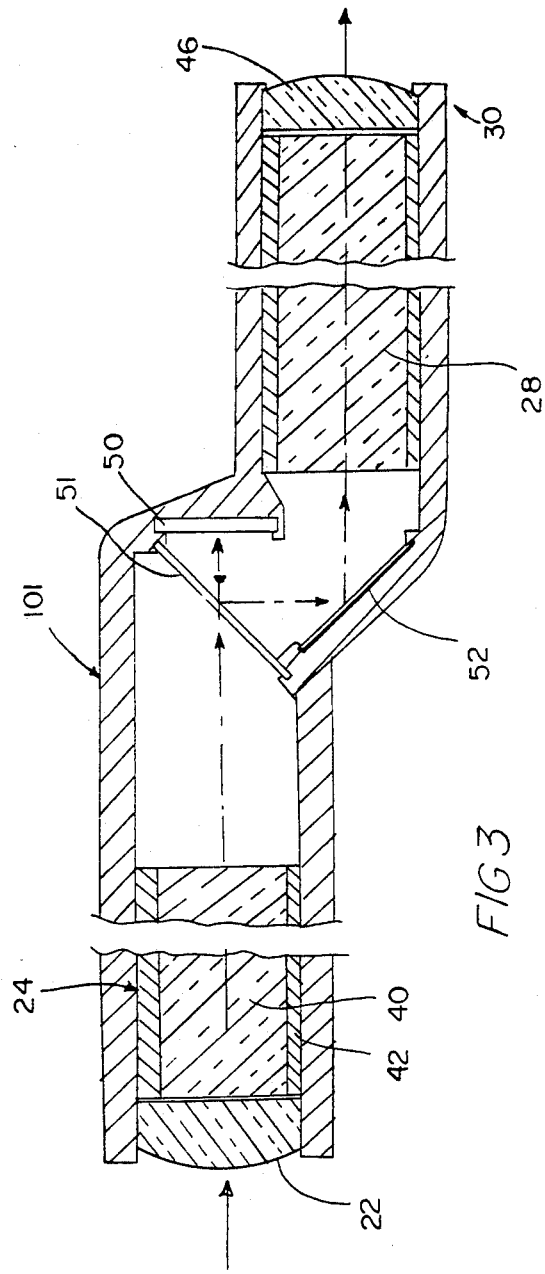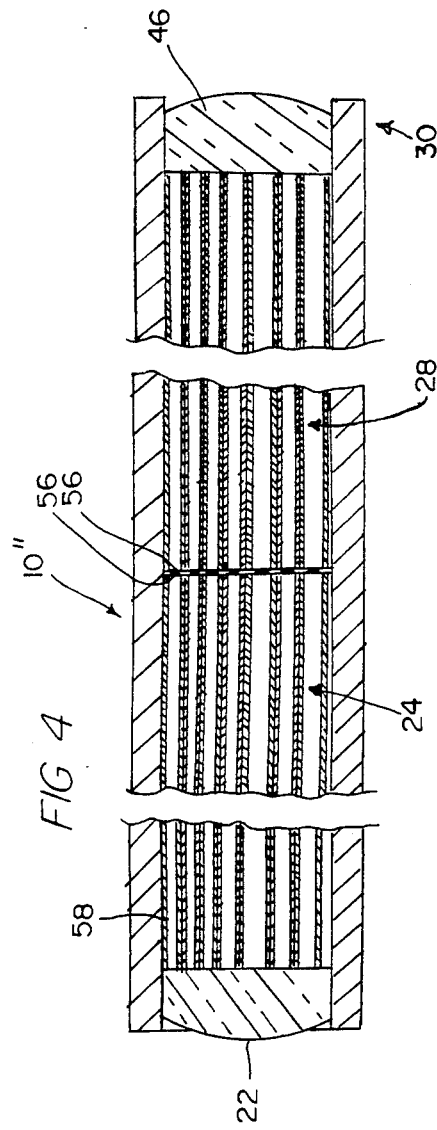

IMAGING ENDOSCOPE AND ENDOSCOPIC METHOD EMPLOYING PHASE CONJUGATE IMAGING TECHNIQUES

BACKGROUND OF THE INVENTION

1. Field of the Invention

This invention relates to improved endoscopes and endoscopic methods employing phase conjugate imaging techniques.

2. Discussion of the Prior Art

Endoscopic or least invasive surgery has many advantages over conventional "open" surgery. Patients who have undergone endoscopic surgery rather than open surgery experience vastly less trauma and much faster recovery, leading to improvement in quality and reduction in cost of health care. These advantages have spurred extensive development of endoscopes.

The term "endoscope" as used herein refers to an elongated optical probe capable of presenting a visible image of the interior of a body cavity, joint, organ or the like to a surgeon by way of an eyepiece or on a video screen. The endoscope is typically introduced into the body cavity through a bore in another device also typically referred to in the art as an endoscope (or as an endoscope sheath) including a light source as well other bores for introducing surgical instruments, water, air, suction and the like. Endoscopes as optimized for various surgical procedures are referred to as arthroscopes, colonoscopes, bronchoscopes, hysteroscopes, cystoscopes, sigmoidoscopes, laparoscopes and ureterscopes.

Endoscopes typically consist of a distal objective for forming an optical image of the interior of the body cavity, bone, joint or organ, a transfer module (sometimes termed a "relay section") for transmitting the image from the distal end of the probe to its proximal end, and an ocular at the proximal end of the transfer module for presenting the image to an eyepiece, a video camera or the like. Typically the ocular contains the movable focusing components of the endoscope.

The art has for some years sought to develop a suitable disposable endoscope. The surgical requirement of absolute sterility is difficult to satisfy with conventional endoscopes as these complex instruments are not readily amenable to conventional sterilization techniques. The spread of infectious disease is of particular concern and requires that care and caution be employed during the sterilization process. Accordingly there is a strong need for a suitable disposable endoscope, that is, one made sufficiently inexpensively as to be cost effective for disposal after single-patient use.

One of the difficult tasks in designing a satisfactory endoscope is that of designing the transfer module. The transfer module must be capable of transmitting the image formed by the objective to the ocular without significant loss of brightness or sharpness. Early designs included numerous glass refractive elements, each requiring extensive polishing and costly anti-reflection coatings. The high cost of manufacture precludes use of these designs for disposable endoscopes.

Accordingly, it is an object of the invention to provide an endoscope which can be manufactured inexpensively so as to be cost-effective for disposability after single-patient use, while not suffering optical performance losses when compared to conventional endoscopes employing complex designs too costly for disposable, single-patient use.

The angular width of the field of view of an endoscope is equivalent to the solid angle from which light rays are gathered by the objective. Typically it is desired that the field of view be centered about a viewing axis forming an angle to the axis of the elongation of the probe. In this way a greater effective field of view is provided; that is, by rotating the probe about its axis of elongation, the surgeon can scan over a larger effective field of view within a body cavity or the like. In order that the axis of the field of view forms an angle with the axis of the probe, a prism may be disposed at the distal tip of the endoscope. Such prisms typically comprise several internally reflecting surfaces to direct light rays received along the axis of the field of view along the axis of the probe. The manufacture of such prisms has in general involved exacting assembly of several costly glass elements, rendering probes incorporating prisms relatively complex and expensive. It will be apparent that an endoscope with a wide field of view is more useful than one with a narrow field of view. Accordingly, it is an object of the invention to provide an endoscope having a relatively wide field of view without requiring a prism at the distal tip of the endoscope probe and eliminating any necessity of rotating the endoscope.

As examples of prior art endoscope probes illustrating one or more of the deficiencies of the prior art mentioned above, reference may be made to the following patents.

U.S. Pat. No. 3,257,902 to Hopkins shows an optical system for an endoscope employing a number of cylindrical rod-like glass lenses in the transfer module of the probe. This design has the deficiency that the rod-like lenses are costly to form, as many individual glass surfaces must be separately polished.

U.S. Pat. No. 4,025,155 to Imai shows an improvement on the Hopkins transfer module employing field and relay lenses. The Imai transfer module is also relatively complicated and difficult to construct.

U.S. Pat. No. 4,138,192 to Yamasita shows a forward viewing optical system for an endoscope including a prism as generally discussed above. The Yamasita prism is relatively complex and expensive to manufacture.

U.S. Pat. No. 4,165,917 to Yamasita et al shows objective assemblies for endoscopes which are relatively complex and costly to manufacture.

U.S. Pat. No. 4,168,882 to Hopkins shows an improvement on the original Hopkins transfer module design of U.S. Pat. No. 3,257,902 referred to above. The improved Hopkins design is also unduly complex and expensive.

U.S. Pat. No. 4,195,904 to Yamasita shows a complicated prism structure for providing a retrograde viewing system for endoscopes.

U.S. Pat. No. 4,755,029 to Okabe shows an objective lens for an endoscope including an element formed of a gradient refractive index (GRIN) material. This design reduces the number of elements in the endoscope at the expense of increasing their complexity of manufacture by use of the GRIN material.

Finally, U.S. Pat. No. 4,964,710 to Leiner shows a transfer module for an endoscope using plano-ended glass rods and molded plastic lenses intermediate the glass rods.

More recently, there has been filed commonly-assigned U.S. patent application Ser. No. 07/833,416 in the name of Broome for a disposable endoscope. The disclosure in that patent application is incorporated herein by reference and relates to an endoscope design wherein substantially all elements of the elongated probe having curved surfaces are molded of plastic such that substantially all the glass elements are plano-ended. This design substantially simplifies manufacture of the endoscope and is cost-effective for single-patient disposable use. The Broome design further features a molded plastic prism for increasing the effective field of view of the endoscope without involving a costly multiple-element glass prism. The disposable probe of the Broome endoscope is designed to be used in conjunction with a non-disposable focusing ocular comprising several glass elements. Despite the substantial improvement provided by the Broome design, there remains as always a desire for further simplification and reduction in cost of the endoscope.

The present invention seeks to further simplify the endoscope design disclosed in the aforesaid patent application and other prior art endoscope designs by utilizing phase conjugate imaging techniques. In essence, a phase conjugate optical filter is a device capable of receiving a number of rays at random angles of incidence and redirecting those rays along paths essentially inverse to the paths of the incident rays. A reflective phase conjugate filter reflects the incident rays precisely back along their incident paths, while a transmissive phase conjugate filter retransmits the incoming rays along ray paths making angles of transmission, with respect to a plane of symmetry of the phase conjugate transmissive element, equal to the angles of incidence at which the corresponding incoming rays meet the plane of symmetry.

An example will assist in understanding the operation of a phase conjugate optical filter.

Reflection takes place at an ordinary plane mirror such that the angle of reflection of the exit ray is precisely equal to the angle of incidence of the incident ray. Thus, if one looks in a plane mirror, one's eye detects rays of light from objects having been incident on the mirror at precisely the angle from which the rays were reflected by the mirror. Accordingly, one sees one's own eye in a plane mirror only when directly looking at the mirror; that is, only then is the incident ray at precisely 90° to the surface of the mirror, so that the angles of incidence and reflection are both 90°. Objects off the perpendicular are seen when a ray from the object is incident on the mirror at precisely the same angle as the ray reflected from the mirror meeting one's eye. For this reason it is possible to see objects imaged in a mirror; that is, because there is a precise one-to-one correspondence between the rays incident on the mirror and the rays received by the mirror from one's eye, an image can be formed. When such a one-to-one relation does not exist, an image cannot be formed. For example, when rays from an object are received by the eye from a variety of directions, a diffuse image is formed, such as from frosted glass or a similar diffusive surface.

By comparison, a phase conjugate reflector has the property of reflecting an incident light ray received from substantially any incident angle back precisely along the incident ray path. A bicycle reflector is a simple example of a phase conjugate reflector. Light incident on the bicycle reflector from any direction is reflected back toward the source. Thus, if one is driving a car at night with the headlights illuminated, hence providing a directional beam, one can see the light reflected from a bicycle reflector even though the headlight beam is not perpendicular to the surface of the reflector. It will be intuitively apparent that if the bicycle reflector were replaced by a plane mirror, one would only see reflection of light from one's headlights under very limited circumstances, that is, when the light beam from the headlights happened to be incident on the mirror substantially perpendicular to its surface, so that the reflected light would return essentially along the path of the incident beam.

A bicycle reflector exhibits the phase conjugate property by provision of multiple-faceted reflector structures, wherein three reflecting planes meet at perpendicular angles to one another, forming "internal corners". Such internal corners have the phase conjugate property, i.e., a light ray incident at any angle on an internal corner formed of three reflectors meeting one another at right angles will reflect back along the direction of the incident ray. The same principle is used in radar reflectors commonly mounted on wires or like structures of small cross-section to ensure that a radar receiver "sees" the structure, and in other applications.

The phase conjugate property is also exhibited by certain photorefractive solids and gases under appropriate circumstances. These instances of the phase conjugate property do not involve internal reflection, but involve stimulated periodic spatial variation in the optical characteristics of the medium. For example, phase conjugation can be performed by "stimulated Brillouin scattering" and by "optical 4-wave mixing in non-linear media". See generally Yeh, "Photorefractive Phase Conjugators", *Proceedings of the IEEE,* vol. 80, no. 3, March 1992. This paper fully discusses the theoretical basis of phase conjugation and gives useful examples of materials which can be employed or stimulated to exhibit this property.

The properties of phase conjugators are also discussed in Shkunov et al, "Optical Phase Conjugation", *Scientific American* December 1985, p. 54–59. Shkunov et al provides an example of the property of phase conjugate optical elements. A coherent light beam passed through a diffusive medium such as frosted glass, if reflected from a phase conjugate reflector and passed back through the same medium, regains its original properties.

The only publication known to the present inventor specifically discussing the application of phase conjugate techniques to endoscopes is U.S. Pat. No. 4,928,695 to Goldman et al. Goldman et al disclose a system for treating diseased tissue within the body. An imaging portion of this device involves passing light distally through an endoscope along a first fiber optic. The light is reflected from the body tissue of interest to pass proximally through the endoscope along a second fiber optic, is reflected by a phase conjugate reflector, passes distally back through the second fiber optic, is reflected a second time from the body tissue, and returns proximally through the first fiber optic to be imaged on a viewing screen. The Goldman et al patent is not clear on the precise reasons for this sequence. The presence of the phase conjugate reflector in the image path between the proximal and distal traversals of the second fiber optic by the reflected light serves merely to return any image of the object to the vicinity of the object. No means is shown for forming an image of the object, or for transmitting such an image to an eyepiece or video imaging chip. Accordingly, the disclosure in Goldman et al does not teach a device capable of satisfying the aforementioned objects of the present invention.

As mentioned above, in one form of optical phase conjugation a so-called four-wave mixing technique is employed. This technique requires a coherent light source, i.e., a laser or the equivalent. It would obviously be desired to provide an endoscope not requiring such a complication. Other phase conjugate techniques employ holographic techniques also requiring a coherent light source such as a laser. For example, U.S. Pat. No. 4,921,333 to Brody et al discusses phase contrast image microscopy using optical phase conjugation. Brody employs holographic phase techniques, thus requiring a coherent light source, and relates to imaging of "transparent phase objects". It would seem that such a microscope would not be amenable to endoscopic use.

Other patents directed to the use of phase conjugation for various purposes include U.S. Pat. No. 4,500,855 to Feinberg, U.S. Pat. No. 4,750,818 to Cochran, U.S. Pat. No. 4,927,251 to Schoen, U.S. Pat. No. 4,938,596 to Gauthier et al, U.S. Pat. No. 5,018,852 to Cheng et al and U.S. Pat. No. 5,059,917 to Stevens. None of these patents relate directly to endoscopic imaging, nor appear amenable to satisfaction of the objects of the invention. Finally, U.S. Pat. No. 4,945,239 to Wist et al teaches a transilluminating system for detecting breast cancers and the like employing a phase conjugate technique, apparently to improve the image. The Wist et al device does not appear suitable for endoscopic image formation.

OBJECTS AND SUMMARY OF THE INVENTION

It is therefore an object of the invention to provide an improved method and apparatus wherein the unique properties of phase conjugative optical elements are employed to yield an endoscope of simplicity and low cost, so as to be cost-effective for single-patient disposable use, being readily manufacturable and suffering no performance disadvantage compared to prior optical endoscopes.

It is a further object of the invention to provide a method and apparatus employing phase conjugative optical techniques as above and furthermore providing a relatively wide effective field of view, eliminating any need for complex prisms or the like in endoscopes.

These and other objects of the invention and needs of the art are satisfied by the endoscope of the present invention. An elongated probe includes a first optically transmissive element extending from the distal tip of the endoscope to an intermediate location. A phase conjugative optical filter element is located at the intermediate location, and a second optically transmissive element extends from the intermediate location to the proximal end of the endoscope. The first and second optically transmissive elements are optically identical and are spaced by the phase conjugative element. Therefore, rays exiting the first transmissive element and incident on the phase conjugate filter are retransmitted by the phase conjugate filter along paths inverse to the incident paths. Any distortion or internal reflection experienced by light transmitted along the first transmissive element is effectively reversed during its transmission along the second element. Accordingly, light rays exit the proximal tip of the endoscope probe bearing the precise relationship to one another as that obtained upon their entry at the distal tip. Conventional image formation techniques can be employed to form an image on an eyepiece or video chip juxtaposed to the proximal end of the endoscope, that is, essentially as if the image were being formed at the distal tip of the endoscope.

An endoscope including a phase conjugate element according to the invention may include objective and ocular lenses of identical optical properties at the proximal and distal tips of the probe, respectively. Such lenses would typically serve to increase the light gathering power of the probe. Intermediate lenses may be disposed on either side of the phase conjugate element and must be optically identical. The first and second transmissive elements may each include a single optical fiber having a core and a cladding meeting at a distinct interface; a bundle of optical fibers; or a plurality of glass rods interspersed with molded glass lenses as, for example, described in the aforementioned Broome patent application. However, in each case the first and second transmissive elements must be optically identical in order that the phase conjugate element can in effect optically invert light rays entering the distal tip of the probe and retransmit the rays to the proximal end of the probe. Identical transmissive paths are thus provided so that light traverses the transmissive paths in a manner optically equivalent to passing the light beams twice through the same optical medium, e.g., as in the example from the Shkunov article, supra.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 1 is a view in longitudinal section of an endoscope according to the invention extending from a portal in a patient's body to a surface of an interior organ or the like to be imaged, together with associated equipment for forming a visible image.

FIG. 2 is an enlarged broken view in longitudinal section of the endoscope probe of FIG. 1 illustrating paths of the optical rays therein.

FIG. 3 is a broken view in longitudinal section of a further embodiment of the invention employing a reflective phase conjugate element.

FIG. 4 is a broken view in longitudinal section of a further embodiment of the invention employing "binary optic" phase conjugate elements.

DESCRIPTION OF THE PREFERRED EMBODIMENTS

A first embodiment of an endoscope 10 employing phase conjugate imaging techniques according to the invention is shown in FIG. 1. Endoscope 10 comprises an elongated tube extending into a body cavity indicated generally at 12 through a portal 14, so that the distal tip of the endoscope is juxtaposed to an internal body part, organ, bone or the like to be examined, as indicated generally at 16. A light source 18 may be integrated with the endoscope probe 10 as shown, or may be provided separately. As indicated above, the endoscope of the invention may slide within a bore in a larger instrument, possibly also including bores for surgical instruments, irrigation, suction, or the like. In the embodiment shown, power for light source 18 is provided by power supply 20. The light emitted by source 18 is incoherent; that is, light source 18 need not comprise a laser or similar source of coherent radiation. Accordingly, light from source 18 is emitted over a wide angle of illumination and is reflected in numerous different directions from the object, i.e., from body part 16. It is the function of the endoscope to collect these dispersed light rays such that a visible image can be formed.

An objective lens 22 may be provided at the distal tip of the endoscope to gather light rays from the object. However, contrary to conventional teachings of the art, objective lens 22 is not required to form an image of the object at or near the distal tip of the endoscope. The image may be formed directly on a charge-coupled diode (CCD) chip 34 for generating a video signal for display. If an objective lens 22 is provided, an optically identical ocular lens 46 must be provided, so that the light transmissive paths are optically identical. Optionally, light exiting the proximal tip of the endoscope is transferred to a second ocular lens 32 at the ocular or proximal end of the endoscope. Optional ocular lens 32 forms an image by focusing light rays onto an eyepiece (not shown) for direct viewing, or onto CCD chip 34. Ocular lens 32 may also be employed to scale the image to the active surface of chip 34, or to collimate the rays so as to appear at infinity for convenience in direct viewing.

Thus, according to the present invention, light reflected from the body part 16 need not be imaged at the distal tip of the endoscope probe as in the prior art. That is, in the prior art, an objective lens forms an image at the distal tip of the endoscope; a transfer module transfers the image from the distal tip to the proximal end, typically forming intermediate images at several points along the length of the probe; and an ocular presents the image to an eyepiece, video imaging chip or the like. According to the present invention, while a lens 22 as shown may be provided at the distal tip of the endoscope 10 to improve the light gathering properties of the endoscope, an image per se is not necessarily formed at the tip of the endoscope.

According to the invention, light rays enter the distal tip of the endoscope 10 from all directions within a wide solid angle, such that a prism is not required to provide a wide field of view. Rays entering the endoscope at its distal tip traverse first transmissive element 24 and are redirected along an inverse path by phase conjugate filter 26. Rays transmitted through filter 26 pass along a second transmissive member 28 to the proximal tip 30 of the endoscope 10. The rays of light exiting the proximal tip 30 will form an identical image of the object without an ocular lens. As mentioned, an ocular lens 32 at proximal tip 30 may be used to focus the rays to form an appropriately sized image on CCD chip 34. CCD chip 34 provides an output signal to a video driver 36, providing a conventional video signal to a video display 38. Ocular lens 32 may also collimate the light rays exiting the proximal tip 30 of the endoscope, so as to provide an image appearing at infinity when directly viewed by means of an eyepiece.

As noted, the first and second transmissive members 24 and 28 must be identical, and may each comprise a single fiber optic having a core 40 and a cladding 42 as shown. Alternatively members 24 and 28 may each comprise a bundle of relatively smaller fiber optics (as discussed in connection with FIG. 4), or a series of rods and lenses as exemplified generally by the prior art referred to above and preferably as disclosed in the Broome patent application Ser. No. 07/833,416. The basic function of the transmissive members 24 and 28 is simply to carry the light rays entering the distal tip of the endoscope to the intermediate phase conjugate filter 26 and thence to the proximal tip 30 with minimum loss in brightness and definition while providing substantially identical optical properties. As mentioned above, if an objective lens 22 is provided, an optically identical lens 46 must be provided to ensure the light transmissive paths on either side of the phase conjugate element are optically identical.

As mentioned, light rays reaching the intermediate phase conjugate filter 26 do not necessarily define an intermediate image but travel in numerous directions determined by the angles of the rays entering the distal tip of the endoscope and the optical characteristics of the transmissive member 24. See FIG. 2, showing in essentially schematic form the random directions of rays entering first transmissive member 24. Such essentially unfocused, random rays traverse transmissive member 24 and enter a transmissive phase conjugate filter 26. As discussed above, a phase conjugate filter has the unique property of emitting rays precisely optically inverse to the incident rays. In the case of a reflective phase conjugate filter (such as a bicycle reflector), the rays are emitted precisely along the path of the corresponding incident rays; in the case of the phase conjugate transmissive filter 26, the angle of exit of the transmitted rays with respect to a plane of symmetry 44 (FIG. 2) is precisely the same as the angle of incidence of the incident rays on plane 44. Therefore, rays exiting the phase conjugate transmissive filter 26 are the "inverse" of those incident on phase conjugate transmissive filter 26.

Accordingly, when the rays exiting filter 26 then traverse a second transmissive member 28 optically identical to the first transmissive member 24, the rays exit the proximal end 30 of the endoscope bearing precisely the same relation to one another as had obtained upon their incidence on the distal tip of the endoscope. Therefore, ocular lens 32 (if employed) may be effectively optically identical to an objective lens for disposition at the distal tip of the endoscope; that is, lens 32 may be designed as if the ocular lens 32 and CCD chip 34 were disposed at the distal tip of the endoscope. Ocular lens 32 may be provided with axial positioning adjustment means (not shown) for focusing the image on chip 34. Ocular lens 32 and chip 34 may also be provided with angular positioning adjustment means (not shown), to scan the entire hemisphere of the object field 16.

As noted, an endoscope employing a phase conjugate transmissive member according to the invention thus requires that the optical paths between the distal tip of the endoscope and the phase conjugate filter 26 and between filter 26 and the ocular lens 32 be identical. Accordingly, if an objective lens 22 is used to gather additional light (or to form an image), an optically identical lens 46 must be disposed at the proximal tip of the endoscope. Likewise, if it is found convenient to employ a lens 48 between the first transmissive member 24 and the phase conjugate filter 26, an optically identical lens 50 must be disposed between the phase conjugate filter 44 and the second transmissive member 28. Lenses 48 and 50 may be useful, for example, to match the effective apertures of the transmissive members 24 and 28 to the aperture of the phase conjugate transmissive member 44.

FIG. 2 shows optical rays entering the endoscope 10 through an objective lens 22 and passing through a first transmissive member 24, again configured as a single fiber optic member having a core 40 and a cladding 42. Rays reflect at various points along the interface between the core and the cladding as shown. The rays then enter phase conjugate transmissive filter 26 and are effectively optically inverted. Rays exiting filter 26 then enter a second transmissive member 28, optically identical to the first transmissive member 24, along ray paths making precisely the same exit angle with respect to the plane of symmetry 44 of filter 26 as made by the incident rays from transmissive member 24. Accordingly, if a lens 46 optically identical to the objective lens 22 is placed at the proximal tip 30 of the endoscope 10, rays exiting the endoscope will have precisely the same relation to one another as the rays entering the endoscope and accordingly can be imaged on the surface of CCD chip 34 to provide a suitable video signal. CCD chip 34 could be replaced by a conventional eyepiece, as is conventional in the art. Again, it will be appreciated that the object 16 viewed by objective lens 22 will be imaged exactly by lens 46 at the proximal tip of the endoscope, without the necessity of optional ocular lens 32.

FIG. 3 shows a further embodiment of the invention wherein the endoscope 10' includes a reflective phase conjugate element 50, a one-way mirror 51 and a plane mirror 52. In this embodiment of the invention, the first transmissive element 24 is off-axis with respect to the second transmissive element 28, while the reflective phase conjugate filter 50, one-way mirror 51 and plane mirror 52 are disposed such that rays are directed correctly from the first transmissive element 24 to the second 28. That is, light rays exiting transmissive member 24 pass through one-way mirror 51, are incident on and are redirected by reflective phase conjugate element 50, reflect from one-way mirror 51 and plane mirror 52, and enter second transmissive member 28. The transmissive elements 24 and 28 must again be optically identical; if an objective lens 22 is used an optically identical lens 46 must be provided at the ocular. In order that the optical path lengths between transmissive elements 24 and 28 and reflective phase conjugate element 50 are identical, element 24 is spaced axially from phase conjugate element 50, as shown. Similarly, if lenses are disposed between the transmissive elements 24 and 28 and the phase conjugate reflective filter and mirror 52 respectively, these too must be optically identical. As indicated above, the transmissive elements 24 and 28 may be solid fiber optic members having a core 40 and a cladding 42 as shown, may comprise a bundle of optical fibers, or may be a sequence of rods and intermediate lenses preferably as discussed in the aforementioned Broome patent application.

As discussed above, the prior art shows a number of different types of phase conjugate optical elements, many of which may be adapted for employment in the several embodiments of the endoscope of the invention. As also indicated above, the preferred embodiment of the invention includes a passive phase conjugate optical filter element, that is, a filter not requiring excitation by a laser beam or the like, as found in certain four-wave mixing phase conjugate elements, or in phase conjugate elements employing Brillouin scattering. Accordingly, solid crystals of phase conjugate materials are in general to be preferred for the phase conjugate filter, whether disposed in a transmissive or reflective configuration.

A further phase conjugate filter suitable for practice of the invention employs so-called "binary optic" technology. See Veldkamp et al, "Binary Optics", *Scientific American*, May 1992, p. 92-97. As discussed by Veldkamp et al, binary optic elements are thin film optical elements employing diffraction rather than refraction for appropriately bending light beams. Binary optic fabrication technology uses the same sequence of masking, reacting, and etching of planar members used to form electronic circuit elements, and many of the same semi-conductor materials. See U.S. Pat. No. 4,895,790 to Swanson et al. Preliminary design studies indicate that binary optic elements can be fabricated to perform the functions of phase conjugate filters. Moreover, the binary optic elements can be fabricated directly on the ends of a bundle of fiber optic elements making up the first and second transmissive members. Alternatively, the binary optic phase conjugate filters can be assembled to a bundle of such fiber optic elements. An exemplary design of an endoscope probe employing such a binary optic phase conjugate filter is shown in FIG. 4.

Referring to FIG. 4, in a further embodiment of endoscope 10", phase conjugate imaging is performed by a plurality of binary optic elements 56 formed on either or both opposed ends of pairs of fiber optic elements 58 formed into bundles so as to collectively constitute the first and second transmissive elements 24 and 28. As indicated by Veldkamp et al, supra, it is possible to form such binary optic elements 56 directly on the ends of fiber optics 58 and then bundle the fiber optics together to form the transmissive members. The binary optic elements may be fabricated on a planar member with the planar member disposed between the opposed ends of the bundles of fiber optics. The binary optic elements may also be fabricated as reflective rather than transmissive phase conjugate members. Diffractive binary optic lenses can also be employed in place of refractive lenses 22, 48, 50, 46 and 32. See Veldkamp U.S. Pat. No. 4,994,664.

The transmissive elements can also comprise solid rods with binary optic members between adjacent rods, that is, in lieu of the intermediate lenses between rods as disclosed in the Broome patent application incorporated by reference above. It is also within the scope of the invention to employ plural phase conjugate filters at spaced locations along the endoscope probe, for example, to limit distortion along a lengthy bundle of fiber optics.

Each of these alternatives is considered to be within the scope of the invention where technically feasible and where not excluded by the scope of the appended claims. Therefore, inasmuch as the present invention is subject to many variations, modifications and changes in detail, it is intended that all subject matter discussed above or shown in the accompanying drawings be interpreted as illustrative only and not be taken in a limiting sense.

What is claimed is:

1. In combination, an elongated endoscope probe for phase conjugate image formation at a proximal end of the probe, and a source of illuminating radiation disposed to illuminate an object near a distal tip of the probe, said probe comprising:

a first transmissive member extending from the distal tip of said probe to a filter location intermediate the distal tip of said probe and the proximal end of said probe;

a second transmissive member extending from said intermediate filter location to the proximal end of said probe, wherein said first and second transmissive members exhibit substantially identical optical transmission characteristics; and a phase conjugate filter disposed at said intermediate filter location, between said first and second transmissive members.

2. The combination of claim 1, wherein said probe further comprises objective and ocular refractive lenses disposed in juxtaposition to the distal tip and proximal end of said elongated probe respectively, said objective and ocular lenses being optically substantially identical.

3. The combination of claim 1, further comprising substantially identical refractive lens elements symmetrically disposed on respective opposite sides of said phase conjugate filter at said intermediate filter location.

4. The combination of claim 1, wherein said illuminating radiation provided by said source is not coherent.

5. The combination of claim 1, wherein said first and second transmissive members each comprise a single fiber optic member.

6. The combination of claim 1, wherein said first and second transmissive members each comprise a bundle of fiber optic members.

7. The combination of claim 1, wherein said phase conjugate filter is a transmissive member having first and second opposite sides and a plane of symmetry, whereby each light ray entering said filter from said first side at an angle of incidence with respect to said plane of symmetry is retransmitted by said filter from said second side along a ray path making the identical exit angle with respect to said plane of symmetry.

8. The combination of claim 1, wherein said phase conjugate filter is a reflective filter reflecting incident rays along their angle of incidence.

9. The combination of claim 8, in further combination with a mirror juxtaposed to said reflective phase conjugate filter to direct said reflected rays along an optical axis of the endoscope.

10. The combination of claim 1, wherein said phase conjugate filter comprises one or more binary optic elements diffracting light incident on said filter so as to provide phase conjugate filtering to the incident light.

11. The combination of claim 10, wherein said binary optic diffractive elements are formed on the ends of a plurality of fiber optic members forming one or both of said first and second transmissive members.

12. The combination of claim 1, wherein said phase conjugate filter is a solid member of a material exhibiting phase conjugate optical properties.

13. The combination of claim 1, in further combination with an ocular lens disposed at the proximal end of said probe for forming an image of an object juxtaposed to said distal tip of said probe.

14. The combination of claim 13, in further combination with means for displaying said image.

15. The combination of claim 14, wherein said means for displaying said image is a video display.

16. A method of forming a visible image of an object in an interior of a body cavity, comprising the steps of:
illuminating the object;
collecting light reflected from the object;
transmitting said light from a distal end of an endoscope extending into said cavity proximally along said endoscope to an intermediate filter location;
employing a phase conjugate filter element disposed at said intermediate filter location to redirect said light;
retransmitting said redirected light proximally along said endoscope to a proximal end thereof; and
forming a visible image of the object.

17. The method of claim 16, comprising the further step of employing two optically identical transmission members, one disposed between said distal end of said endoscope and said intermediate filter location, and one disposed between said intermediate filter location and said proximal end thereof, to perform said transmitting and retransmitting steps.

18. The method of claim 16, wherein said phase conjugate filter element is a transmissive element having first and second sides and a plane of symmetry, whereby said element redirects light rays entering said element from said first side at a particular angle to said plane of symmetry of said element, such that said rays exit said element from said second side along ray paths forming the identical angle with respect to said plane of symmetry.

19. The method of claim 16, comprising the further steps of disposing a lens at said distal end of said endoscope, to perform said step of collecting light, and disposing a further substantially identical lens at the proximal end of said endoscope.

20. The method of claim 16, wherein said step of forming a visible image of the object includes the steps of focusing light transmitted to said proximal end of said endoscope onto an image plane, disposing a video signal forming device in said image plane to form a video signal responsive to said focused light, and employing said video signal to drive a video display.

* * * * *